(12) United States Patent
Kim et al.

(10) Patent No.: US 11,365,388 B2
(45) Date of Patent: Jun. 21, 2022

(54) MICROORGANISM HAVING MINIMAL GENOME AND METHOD OF PRODUCING THE SAME

(71) Applicants: Intelligent Synthetic Biology Center, Daejeon (KR); Korea Advanced Institute of Science and Technology, Daejeon (KR)

(72) Inventors: Sun-Chang Kim, Daejeon (KR); Byung-Kwan Cho, Daejeon (KR); Donghui Choe, Daejeon (KR); Bong Hyun Sung, Daejeon (KR); Jun Hyoung Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 56 days.

(21) Appl. No.: 16/751,986

(22) Filed: Jan. 24, 2020

(65) Prior Publication Data
US 2020/0239831 A1    Jul. 30, 2020

(30) Foreign Application Priority Data
Jan. 28, 2019   (KR) .................. 10-2019-0010539

(51) Int. Cl.
| | | |
|---|---|---|
| *C12N 1/20* | (2006.01) | |
| *C12P 7/46* | (2006.01) | |
| *C12P 21/02* | (2006.01) | |
| *C12R 1/19* | (2006.01) | |

(52) U.S. Cl.
CPC .............. *C12N 1/20* (2013.01); *C12N 1/205* (2021.05); *C12P 7/46* (2013.01); *C12P 21/02* (2013.01); *C12R 2001/19* (2021.05)

(58) Field of Classification Search
CPC ....................................................... C12P 7/46
See application file for complete search history.

(56) References Cited

FOREIGN PATENT DOCUMENTS

| KR | 2014-0141228 A | 12/2014 |
| KR | 10-1528943 B1 | 6/2015 |
| WO | 2015/042105 A1 | 3/2015 |

OTHER PUBLICATIONS

Hermann et al., "Haemodynamic effects of intracoronary pyruvate in pateints with congesitve heart failure: an open study", Lancet, 1999, 353: 1321-23.
Hutchison, et al., "Design and synthesis of a minimal bacterial genomre", Science, Mar. 25, 2016, vol. 351, Issue 6280, pp. aad6253-1-aad6253-11.
Jaimes et al., "Functional response of the isolated, perfused normoxic heart to pyruvate dehydrogenase activation by dichloroacetate and pyruvate", Pflugers Arch., Jan. 2016, 468(1): 131-142.
Choe, Donghui et al., "Adaptive laboratory evolution of a genome-reduced *Escherichia coli*", Nature Communications, vol. 10, No. 1, Feb. 25, 2019.
Keun, Myung et al., "Enhancing recombinant protein production with an *Escherichia coli* host strain lacking insertion sequences", Applied Microbiology and Biotechnology, vol. 98, No. 15, Apr. 22, 2014, pp. 6701-6713.
Stoyanov, Borislav, European Search Report, European Patent Office, Application No. 20153976.4, dated May 26, 2020.

*Primary Examiner* — Bin Shen
(74) *Attorney, Agent, or Firm* — Gavrilovich, Dodd & Lindsey LLP (57) ABSTRACT

Provided is a method of producing a novel microorganism having a minimal genome. In particular, provided are a method of producing a novel microorganism having a smaller genome size than a wild-type, the method including the step of culturing the microorganism in a medium containing LB broth with stepwise decreasing concentrations of the LB broth; and a novel microorganism having a smaller genome size than a wild-type, produced by the above method.
Despite the small genome size, the novel microorganism of the present disclosure may have a high growth rate, pyruvate production capacity, and protein translation efficiency thereby being usefully applied to industry such as production of recombinant proteins or pyruvate.

10 Claims, 9 Drawing Sheets

Specification includes a Sequence Listing.

*FIG. 13C*

SEQUENCE LISTING

<160> NUMBER OF SEQ ID NOS: 8

<210> SEQ ID NO 1
<211> LENGTH: 38
<212> TYPE: DNA
<213> ORGANISM: Artificial Sequence
<220> FEATURE:
<223> OTHER INFORMATION: MutS_Tn_F

<400> SEQUENCE: 1
gcatattggc tcgaattcca accgatacaa ttttgcgt                    38

<210> SEQ ID NO 2
<211> LENGTH: 35
<212> TYPE: DNA
<213> ORGANISM: Artificial Sequence
<220> FEATURE:
<223> OTHER INFORMATION: MutS_neo_R

<400> SEQUENCE: 2
taataagggg atcttttaca ccaggctctt caagc                       35

<210> SEQ ID NO 3
<211> LENGTH: 35
<212> TYPE: DNA
<213> ORGANISM: Artificial Sequence
<220> FEATURE:
<223> OTHER INFORMATION: MutS_neo_F

<400> SEQUENCE: 3
aagagcctgg tgtaaaagat cccttatta gaaga                        35

<210> SEQ ID NO 4
<211> LENGTH: 38
<212> TYPE: DNA
<213> ORGANISM: Artificial Sequence
<220> FEATURE:
<223> OTHER INFORMATION: Neo_Tn_R

<400> SEQUENCE: 4
ctgcaggtcg actctagaag agcgcttttg aagctcac                    38

<210> SEQ ID NO 5
<211> LENGTH: 28
<212> TYPE: DNA
<213> ORGANISM: Artificial Sequence
<220> FEATURE:
<223> OTHER INFORMATION: Me_plus_3'

<400> SEQUENCE: 5
ctgtctctta tacacatctc aaccatca                               28

<210> SEQ ID NO 6
<211> LENGTH: 28
<212> TYPE: DNA
<213> ORGANISM: Artificial Sequence
<220> FEATURE:
<223> OTHER INFORMATION: ME_plus_5'

<400> SEQUENCE: 6
ctgtctctta tacacatctc aaccctga                               28

<210> SEQ ID NO 7
<211> LENGTH: 25
<212> TYPE: DNA
<213> ORGANISM: Artificial Sequence

```
<220> FEATURE:
<223> OTHER INFORMATION: TN_confirm_F

<400> SEQUENCE: 7
gacgggacgg cggctttgtt gaata                                              25

<210> SEQ ID NO 8
<211> LENGTH: 46
<212> TYPE: DNA
<213> ORGANISM: Artificial Sequence
<220> FEATURE:
<223> OTHER INFORMATION: Random_R1
<220> FEATURE:
<221> NAME/KEY: misc_feature
<222> LOCATION: (34)..(41)
<223> OTHER INFORMATION: n is a, c, g, or t

<400> SEQUENCE: 8
ctcggcattc ctgctgaacc gctcttccga tctnnnnnnnn ngctgg                      46
```

MICROORGANISM HAVING MINIMAL GENOME AND METHOD OF PRODUCING THE SAME

CROSS REFERENCE TO RELATED APPLICATIONS

This application is filed under 35 U.S.C. 119 and claims priority to Korean Application No. 10-2019-0010539, filed Jan. 28, 2019, the disclosure of which is incorporated herein by reference.

FIELD OF THE INVENTION

The present disclosure relates to a novel microorganism having a minimal genome, a method of producing the same, and a method of producing a useful product using the same.

BACKGROUND OF THE INVENTION

Description of the Related Art

Minimal genomes, which include only the necessary genes to maintain self-replicable life, have been studied. For example, a 1.08-Mbp *Mycoplasma mynoides* genome and its re-designed version (JCVI-syn3.0), called "bottom-up" approach, were generated by de novo genome synthesis. The redesigned genome was transplanted into a similar bacterial strain, *Mvycoplasmna capricolum* to successfully create a viable organism (Science. 2016 Mar. 25; 351 (6280): aad6253).

In such a genome design, a top-down approach has been also used, in which sequential genome reduction occurs in rich media without growth retardation. In this regard, the above-mentioned method was applied to develop a new microorganism producing 1,2-propanediol (Korean Patent No. 10-1528943).

However, there is a disadvantage in that when genome-reduced strains are grown in minimal medium without any nutrient supplementation, their growth rate is reduced. The decreased growth rate has been attributed to limited understanding of some bacterial genome processes, such as synthetic lethality and interactions between interconnected cellular components. Therefore, the above-described sequential method has made it difficult to construct a useful minimal genome that may be used for research or as a highly industrially available strain.

Under this background, the present inventors have made intensive efforts to develop a novel microorganism having a minimal genome while having high industrial availability, and as a result, they have produced a novel microorganism having a smaller genome size than a wild-type through adaptive laboratory evolution (ALE) of using LB broth and a concentration gradient thereof, and they found that, despite the small genome size, the novel microorganism has high protein translational efficiency, and high pyruvate production capacity, as compared with the wild-type, without reduction in the growth rate, thereby completing the present disclosure.

SUMMARY OF THE INVENTION

An object of the present disclosure is to provide a novel microorganism having a minimal genome.

Another object of the present disclosure is to provide a method of producing the novel microorganism.

Still another object of the present disclosure is to provide a method of producing pyruvate or a protein using the novel microorganism.

BRIEF DESCRIPTION OF THE DRAWINGS

FIG. 1A-B is a graph showing growth profiles of MG1655 and MS56, in which

FIG. 12A-C shows the result of genome sequencing of eMS57, in which FIG. 13A-C shows the result of transcriptome analysis of eMS57, in which

DETAILED DESCRIPTION OF THE PREFERRED EMBODIMENTS

To achieve the objects above, one aspect of the present disclosure provides a novel microorganism having a smaller genome size than the wild-type.

The present inventors have developed a novel microorganism that overcomes a disadvantage of low growth efficiency of existing E. coli having a reduced genome, wherein despite the reduced genome, the novel microorganism has high growth efficiency, has high protein production capacity due to high mRNA translational efficiency, and has high pyruvate production capacity. The novel microorganism provided in the present disclosure may be very usefully used as a host for the production of a desired protein and pyruvate.

The novel microorganism may be a microorganism deposited with the Accession No KCTC 13699BP. In one embodiment of the present disclosure, E. coli MS56 strain known to have a minimal genome size was cultured in LB broth with stepwise decreasing concentrations. As a result, E. coli strain "eMS57" having a higher growth rate than that of MS56 strain and having a cell growth rate equivalent to that of the wild-type was prepared (FIG. 4), and this strain was deposited at the Korean Collection for Type Cultures, Korea Research Institute of Bioscience and Biotechnology on Nov. 8, 2018 with the Accession No KCTC 13699BP.

This novel microorganism is characterized by having a smaller genome size than the wild-type. Specifically, the genome size may be 3.5 Mbp to 3.7 Mbp.

At present, the wild-type E. coli strain is known to have the genome size of about 4 Mbp to about 6 Mbp. In contrast, a microorganism having a minimal genome is E. coli strain "MS56", which is known to have the size of about 3.6 Mbp (Appl Microbiol Biotechnol. 2014 August; 98(15):6701-13). Since the microorganism strain of the present disclosure is derived from the MS56 strain, it has a genome size similar thereto. Further, in the novel microorganism according to the present disclosure, a gene decreasing the growth rate due to metabolic burden. Therefore, there are advantages in that the novel microorganism may exhibit characteristics of the increased growth rate, etc., and biotechnological manipulation for the production of a desired product is simple.

In one embodiment of the present disclosure, genome sequencing, transcriptome analysis, and ribosome profiling of the novel microorganism were performed to examine changes in genetic mutations and protein expression levels, as compared with the wild-type strain MG1655. The changes in genetic mutations and/or protein expression levels may be factors indicating the advantages of the novel microorganism of the present disclosure, but are not limited thereto.

In the present disclosure, the novel microorganism may have a higher growth rate than the wild-type.

Specifically, a microorganism having a minimal genome hardly survives without nutrients such as LB broth, etc. In contrast, although the novel microorganism of the present disclosure has the minimal genome, it may exhibit a growth rate and sufficient cell density, which are similar to or higher than the wild-type, even in a minimal medium without any nutrient supplementation.

Further, the novel microorganism may have a higher pyruvate production capacity than the wild-type.

In detail, since pyruvate acts as an intermediate in metabolic pathways in an organism, general microorganisms utilize pyruvate only in the intracellular metabolisms and do not excrete pyruvate extracellularly. In contrast, the novel microorganism of the present disclosure may exhibit higher intracellular pyruvate concentrations and about 9 times or higher extracellular pyruvate concentrations than the wild-type, indicating very excellent pyruvate production capacity.

Meanwhile, in addition to its use in the intracellular metabolisms, pyruvate is known to have pharmacological effects of improving metabolisms by stimulating NADH production and increasing cardiac function (Pflugers Arch 2016 January; 468(1): 131-142; Lancet. 353 (9161): 1321-1323), and pyruvate also has low skin irritation and excellent skin moisturizing effect, and thus it is highly likely to be usefully applied to pharmaceutical and cosmetic compositions. Furthermore, a method of synthesizing sialylactose having excellent efficacy in immune activity, infection prevention, brain development, and cognitive improvement by using pyruvate as a precursor has been recently developed (Korean Patent Application No. 2013-0062733), and thus it is expected that use of pyruvate is further increased.

Further, the novel microorganism may have higher translational efficiency than the wild-type.

Specifically, production of a protein consists of transcription of mRNA from a gene and translation of the protein from the mRNA. Although the transcription process works well and thus the amount of mRNA increases, the protein production efficiency may be reduced by translational buffering. The novel microorganism of the present disclosure exhibits no translational buffering phenomenon, thereby achieving high translational efficiency, and as a result, exhibiting high protein production efficiency.

Lastly, the novel microorganism may be engineered to have a low mutation rate.

Specifically, such a low mutation rate may be achieved by mulS (UniProtKB: P23909, NCBI Gene ID: 947206, etc.) gene, and the novel microorganism of the present disclosure may include the gene.

Further, mutations in microorganisms may cause loss of intrinsic properties of the microorganisms, and may cause harm to humans, particularly, pathogenicity. Further, the novel microorganism of the present disclosure may exhibit useful properties as an industrial strain, as compared with its starting strain or wild-type strain. Thus, it is important to minimize the mutation rate so that the microorganism does not exhibit adverse properties while maintaining its own intrinsic properties.

In the present disclosure, the novel microorganism is any kind of microorganism, as long as it is applicable in the method of the present disclosure. Specific examples may include microorganisms of the genus *Escherichia*, the genus *Serratia*, the genus *Erwinia*, the genus *Enterobacteria*, the genus *Salmonella*, the genus *Streptomyces*, the genus *Pseudomonas*, the genus *Brevibacterium*, or the genus *Corynebacterium*, etc., specifically, microorganisms of the genus *Escherichia*, and most specifically, *E. coli* (*Escherichia coli*).

Figure 11A:
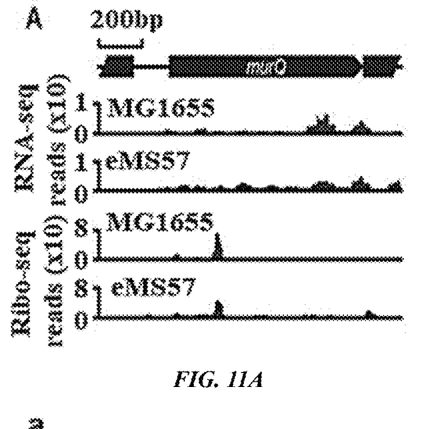
FIG. 11A-B is a chromatogram showing a comparison of RNA-seq and Ribo-Seq profiles, FIG. 11A for murQ gene and FIG. 11B for gapA gene, in which in FIG. 11A, murQ expression levels of MG1655 and eMS57 were 12.18 and 10.20, respectively, translation levels were 16.02 and 9.54, respectively, and translational efficiencies were 1.32 and 0.94, respectively, and in FIG. 13B, gapA expression levels of MG1655 and eMS57 were 3484.22 and 3719.73, respectively, translation levels were 2223.45 and 3213.62, respectively, and translational efficiencies were 0.64 and 0.86, respectively.
Figure 11B:
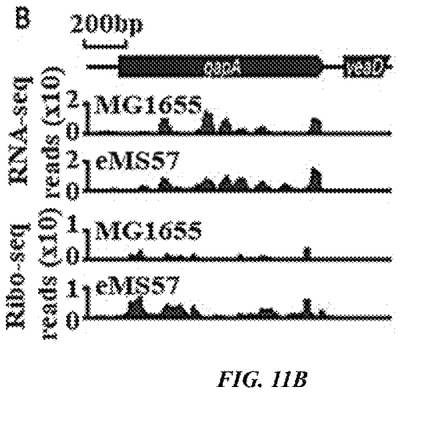

In a specific embodiment of the present disclosure, it was confirmed that the novel microorganism, eMS57 strain excretes about 9 times larger amount of extracellular pyruvate (FIG. 7) and more excellent or similar protein translational efficiency than or to the wild-type strain, depending on the kind thereof (FIG. 11).

These results indicate that the novel microorganism of the present disclosure may be usefully applied in the industry of producing desired products such as proteins, pyruvate, etc. through culturing the microorganism.

Another aspect provides a method of producing the novel microorganism.

In this regard, description of the "novel microorganism" is the same as described above.

As used herein, the term "LB broth" refers to a nutrient composition of a medium which is used in culturing microorganisms, and is also called LB broth, Lysogeny broth, Luria broth, Lennox broth, etc. LB broth generally consists of a yeast extract which is extracted from yeast and contains various nutrients necessary for microorganisms to grow, tryptone which is a protein source, and sodium chloride (NaCl) which prevents the cells to be cultured from osmosis.

Specifically, the LB broth may include 8% (w/v) to 12% (w/v) tryptone, 3% (w/v) to 7% (w/v) yeast extract, and 8% (w/v) to 12% (w/v) NaCl; and more specifically, 10% (w/v) tryptone, 5% (w/v) yeast extract, and 10% (w/v) NaCl, but is not limited thereto.

In the present disclosure, a medium containing the LB broth may be in the form of liquid or solid, and may be readily selected by those skilled in the art in order to produce the novel microorganism of the present disclosure.

Specifically, when the medium is a liquid medium, it may be prepared by mixing each of tryptone, yeast extract, and NaCl in the above range with distilled water, or by mixing a mixture of tryptone, yeast extract, and NaCl in the above range with distilled water, but is not limited thereto. Further, when the medium is a solid medium, it may be prepared by adding an appropriate material, such as gelatin, agar, silica gel, etc., to the liquid medium, but is not limited thereto.

With respect to the objects of the present disclosure, the preparation method is required to include the step of serially culturing the microorganism in a medium containing the LB broth with stepwise decreasing concentrations.

Specifically, the step may be a process of adaptive laboratory evolution (ALE). The ALE is a method used to obtain mutants of a microorganism, in which appropriate stress is applied during growth of the microorganism to cause genotypic and phenotypic changes. The present disclosure aims to produce a microorganism having a minimal genome while having an increased survival rate, thereby producing the microorganism which is efficiently able to survive even in less nutrition by gradually depleting LB broth which is a nutrient component contained in the medium.

Specifically, the decreasing concentrations of the LB broth may be achieved by gradually reducing the concentration to 0.12% (v/v) to 0.08% (v/v), 0.07% (v/v) to 0.03% (v/v). 0.015% (v/v) to 0.005% (v/v), 0.003% (v/v) to 0.001% (v/v), and 0%; and more specifically, (v/v, 0.1% (v/v), 0.05% (v/v), 0.01% (v/v). 0.002% (v/v), and 0%, but are not limited thereto.

Still another aspect of the present disclosure relates to a method of producing pyruvate or a protein, the method including the step of culturing the novel microorganism of the present disclosure.

The media and other culture conditions employed in the culturing are not particularly limited, as long as they are those applicable to culturing the microorganism of the present disclosure, and may be appropriately selected by those skilled in the art, based on the contents known in the art. Specifically, the microorganism of the present disclosure may be cultured in a common medium containing an appropriate carbon source, nitrogen source, and phosphorous source, inorganic compounds, amino acids, and/or vitamins, etc. under aerobic or anaerobic conditions while adjusting temperature, pH, etc.

The preparation method may further include the step of collecting the pyruvate or protein from the medium or the microorganism, after the step of culturing the microorganism.

The collecting step may be to collect the desired material from the culture medium by using an appropriate method known in the art according to the method of culturing the microorganism of the present disclosure, for example, a batch, continuous, or fed-batch culture method.

The collecting step may include a purification process.

Hereinafter, the present disclosure will be described in more detail with reference to Examples. However, these Examples are only for illustrating the present disclosure, and the scope of the present disclosure is not intended to be limited by these Examples Example 1. Production of eMS57 Strain Having Minimal Genome and Excellent Growth Rate To produce a strain having a minimal genome while exhibiting a high growth rate, ALE was used. Specifically, 'MS56' strain having a minimal genome size (about 3.6 Mbp) which was created from the systematic deletion of 55 genomic regions of a wild-type *E. coli* 'MG1655' strain was used as a starting strain of ALE.

Figure 1A:
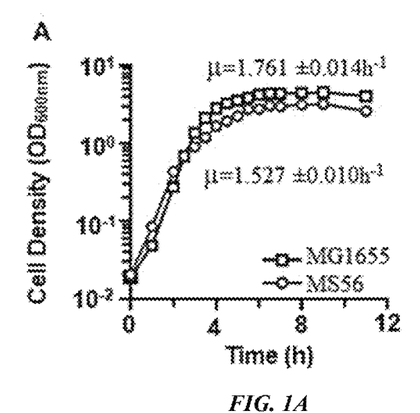
FIG. 1A shows growth profiles in LB medium.
Figure 1B:
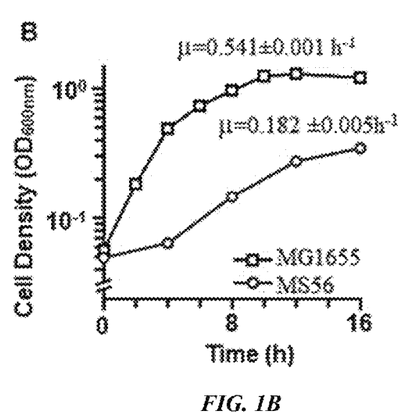
FIG. 1B shows growth profiles in M9 minimal medium, MG1655 indicating a wild-type *E. coli* strain, and MS56 indicating an *E. coli* strain having a minimal genome.

Meanwhile, *E. coli* MS56 was grown in an M9 glucose medium at 37° C. with agitation. Cultures were transferred to fresh medium every 12 hrs at an initial $OD_{600mm}$ of approximately 0.005. The growth rates of MS56 and MG1655 were examined, and as a result, MS56 exhibited a comparable growth rate to MG1655 in a rich medium, but it showed severe growth reduction in a minimal medium (FIG. 1).

Figure 2:
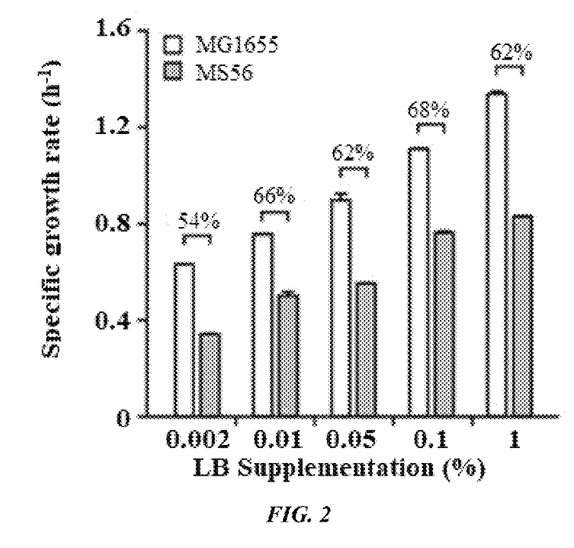
FIG. 2 is a graph showing growth rates of MG1655 and MS56 in LB-supplemented M9 minimal medium.
Figure 3:
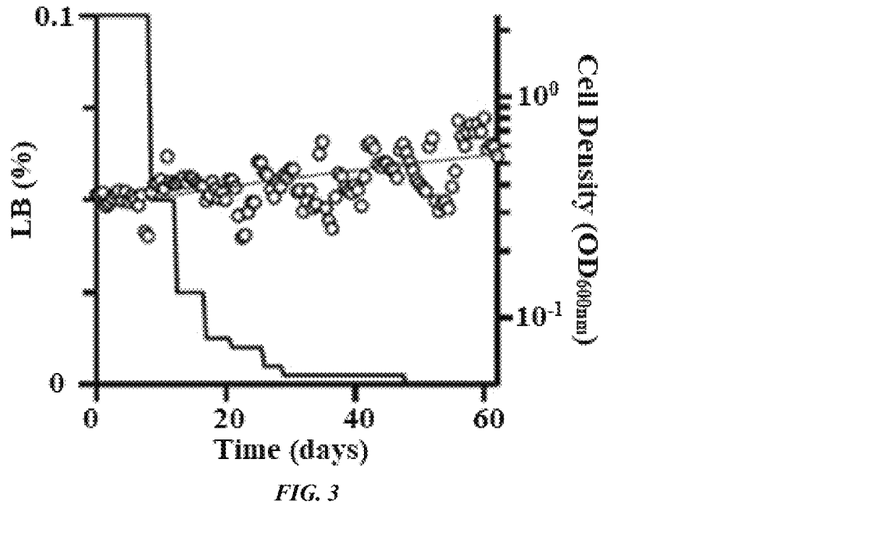
FIG. 3 is a graph showing cell density of MS56 according to LB concentrations and time, in which MS56 adaptively evolved in LB-supplemented M9 minimal medium, and LB supplementation was stepwise reduced from 0.1% to 0% over time.

As described, since MS56 showed the low growth rate in M9 minimal medium, it was intended to produce a strain showing a high growth rate in the minimal medium while having a minimal genome. First, the medium was supplemented with 0.1% (v/v) of LB broth, which restored the growth rate of MS56 to ⅔rds of the level of MG1655 (FIG. 2). Then, LB broth supplementation was reduced to 0.1% (v/v), 0.05% (v/v), 0.01% (v/v), and 0.002% (v/v) in a stepwise fashion to reach LB-free growth (FIG. 3). After 807 generations of ALE (adaptive laboratory evolution), LB was finally removed. Meanwhile, number of cell divisions during ALE was calculated from final and initial cell densities according to the following Equation 1. Meanwhile, the LB broth was prepared by mixing 10 g of tryptone, 5 g of yeast extract, and 10 g of NaCl in 1 L of distilled water.

Number of generation=$\log_2$(final cell density/initial cell density) [Equation 1]

Figure 4:
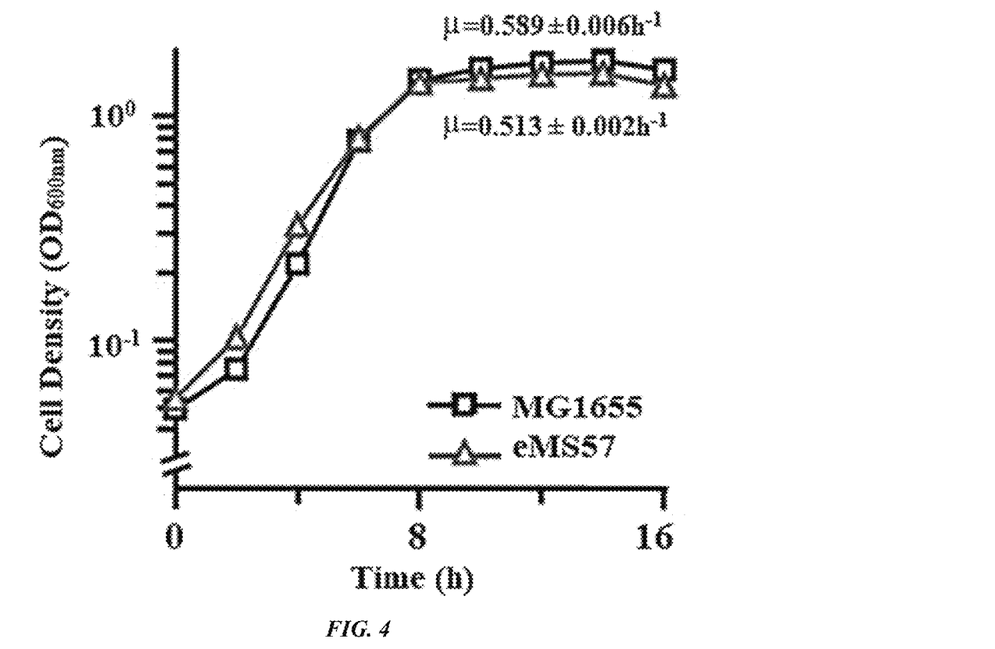
FIG. 4 is a graph showing cell density of eMS57 which is an evolved strain prepared from MS56 through ALE, and MG1655 which is a wild-type strain.

As a result, an evolved strain which restored final cell density and growth rate to levels comparable to MG1655 in M9 minimal medium without LB nutrient supplementation was produced and named 'eMS57' (FIG. 4).

Example 2. Phenotypic Examination of eMS57

For phenotypic examination of eMS57, morphology was compared between eMS57, MS56, and MG1655 using electron microscopy.

1 mL of exponential phase culture was prefixed in 2.5% paraformaldehyde-glutaraldehyde mixture buffered with 0.1 M phosphate buffer (pH 7.2) at 4° C. for 2 hrs. The prefixed sample was treated with 1% osmium tetroxide solution buffered with 0.1 M phosphate buffer (pH 7.2) for 1 hr at room temperature (25° C.). The fixed sample was dehydrated in ethanol, substituted by isoamyl acetate, and critical point-dried in liquid $CO_2$. The sample was finally sputter-coated with gold in a Sputter Coater SC502 (Polaron, Quorum Technologies, East Sussex, UK) to 20 nm thickness, and SEM images were obtained using the FEI Quanta 250 FEG scanning electron microscope (FEI, Hillsboro, Oreg., USA) installed at the Korea Research Institute of Bioscience and Biotechnology at a 10-kV acceleration voltage. For transmission electron microscopy, a sample fixed using the same method as used for SEM imaging was dehydrated in ethanol, substituted with propylene oxide, and embedded in Epon-812 Resin for 36 hrs at 60° C. The embedded sample was ultra-sectioned with an Ultracut E Ultramicrotome (Leica, Wetzlar, Germany) and double-stained with uranyl acetate and lead citrate. The sample was examined under a CM20 transmission electron microscope (Philips, Amsterdam, Netherlands) installed at the Korea Research Institute of Bioscience and Biotechnology at a 100-kV acceleration voltage.

Figure 5:
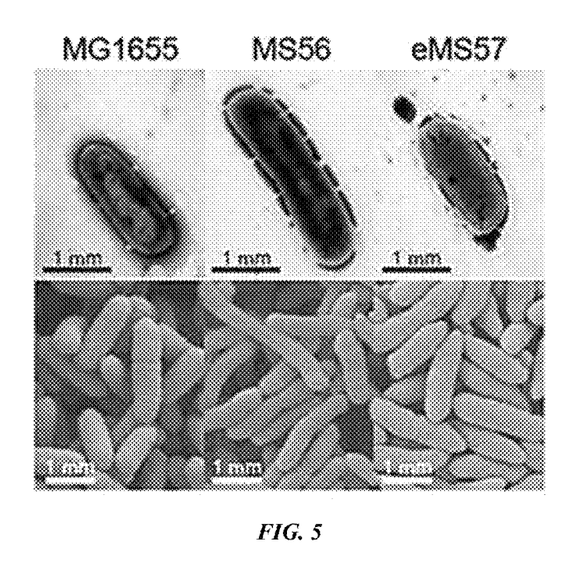
FIG. 5 is an electron microscopy image showing morphological changes between MG1655, MS56, and eMS57.

As a result, it was confirmed that eMS57 had a similar cell size and length to the wild-type MG1655, and a shorter cell length than MS56 having the minimal genome (FIG. 5).

Example 3. Examination of Utilized Nutrient Source

To examine the kinds of nutrient sources utilized by eMS57, characteristics were examined in each strain of eMS57, MS56, and MG1655.

First, phenotype microarray was examined by the following method. Each strain was dispensed on BUG (Biolog Universal Growth) agar, and grown overnight at 37° C. Then, cells were diluted with Inoculating Fluid A (80% IF-0a GN/GP Base) to 42% transmittance. A cell resuspension of 42% transmittance was diluted with 5× Inoculating Fluid B (83.33% IF-0a GN/GP Base and 1.2% Biolog Redox Dye mix A) to generate a cell resuspension of 85% transmittance Thereafter, 19.8 mM of sodium succinate and 1.98 nM of ferric citrate as carbon sources were added to Inoculating Fluid B. and 100 µL of the cell resuspension of 85% transmittance was inoculated onto PM plates and cellular respiration was measured.

Figure 6:
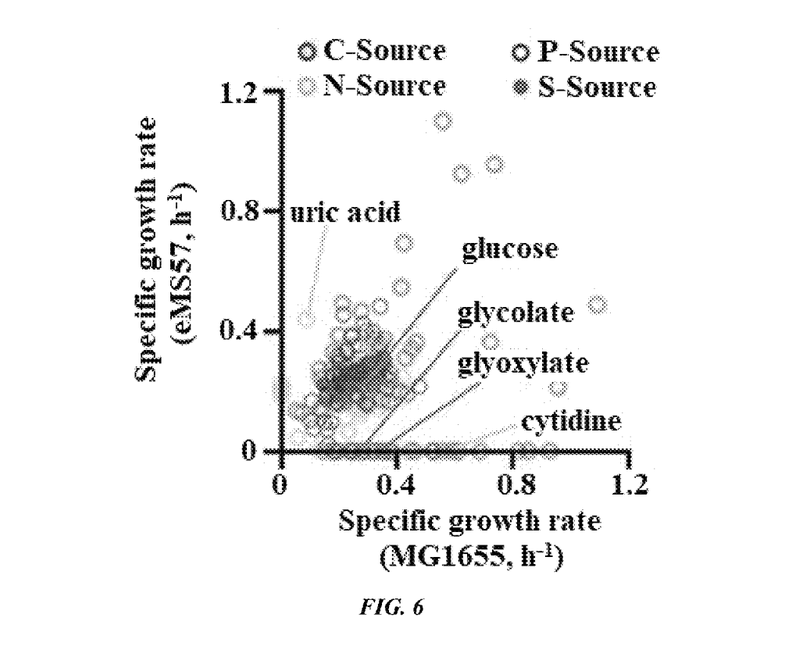
FIG. 6 is a graph showing growth rates under different nutrients, regarding results of phenotype microarray analysis of MG1655 and eMS57.

As a result, eMS57 showed a narrower spectrum of nutrient utilization for carbon, nitrogen, phosphorus, and sulfur sources than MG1655 in terms of respective nutrient utilization (FIG. 6). eMS57 did not show cellular respiration on glycolate and glyoxylate as the sole carbon source. MG655 and eMS57 exhibited different nitrogen utilization preferences, but eMS57 showed no significant change in phosphorus and sulfur source utilization. The growth rate of MG1655 in cytidine was much higher than that of eMS57, whereas eMS57 preferentially utilized uric acid as the sole nitrogen source.

These results indicate that eMS57 utilizes pyruvate as the carbon source and uric acid as the nitrogen source during cellular respiration.

Example 4. Examination of Pyruvate Production Capacity

To examine the pyruvate production capacity of eMS57, characteristics were examined in each strain of eMS57, MS56, and MG1655.

Meanwhile, the pyruvate uptake function was examined by the following method. Each strain was grown in LB medium at 37° C. for 8 hrs, and washed twice with M9 pyruvate medium (M9 minimal medium supplemented with 2 g/l of pyruvate) Then, the washed cells were grown overnight in M9 pyruvate medium at 37° C., and washed twice with M9 sorbitol medium (M9 minimal medium supplemented with 2 g/l of sorbitol), and inoculated in 30 ml of M9 sorbitol medium when initial $OD_{600mm}$ was 0.05. The culture was grown for one doubling ($OD_{600mm}$ of 0.1). Then, each 400 µl of the grown culture was transferred into a 48-well microplate and 3-fluoropyruvate (3-FP) was added to a final concentration of 1 mM. The plate was incubated at 37° C. with shaking, and $OD_{600mm}$ was recorded using a microplate reader (BioTek).

Further, intracellular and extracellular pyruvate production capacity was measured as follows. The strain was grown in M9 glucose medium at 37° C. Then, 1 ml of culture was centrifuged, and the supernatant was collected for analysis of extracellular pyruvate. 5 ml of culture was quenched with 5 ml of quenching solution (40% ethanol; v/v, 0.8% NaCl; w/v) pre-chilled to −35° C. Quenched cells were collected when the temperature reached −5° C. by centrifugation at −11° C. Then, the cell pellet was resuspended with 500 µl pre-chilled to −80° C. The resuspension was frozen and thawed 3 times with liquid nitrogen. Centrifugation was performed, and then supernatant was collected. Methanol extraction was performed to completely extract pyruvate from the pellet. Pyruvate concentration was measured using an EnyChrom™ Pyruvate Assay Kit (Bioassay Systems).

Figure 7:
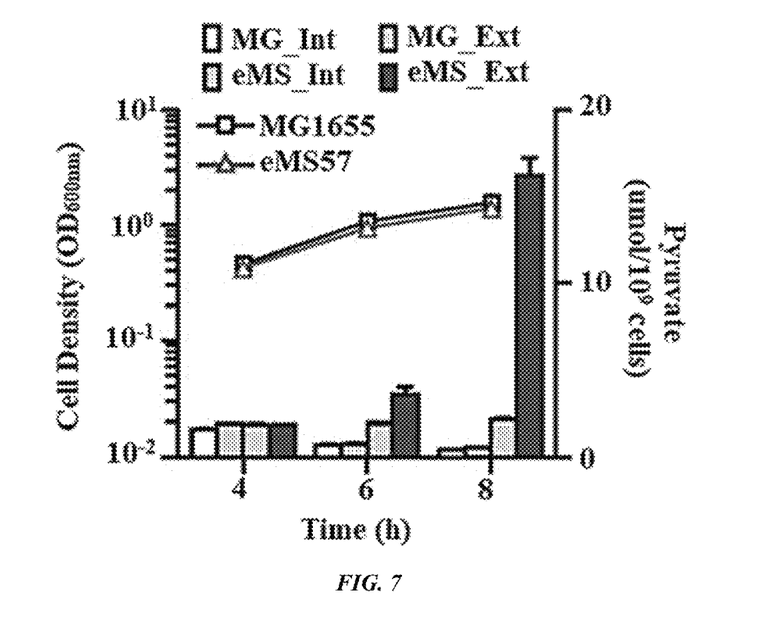
FIG. 7 is a graph showing final cell density of MG1655 and eMG57 and intracellular/extracellular pyruvate concentrations.
Figure 8:
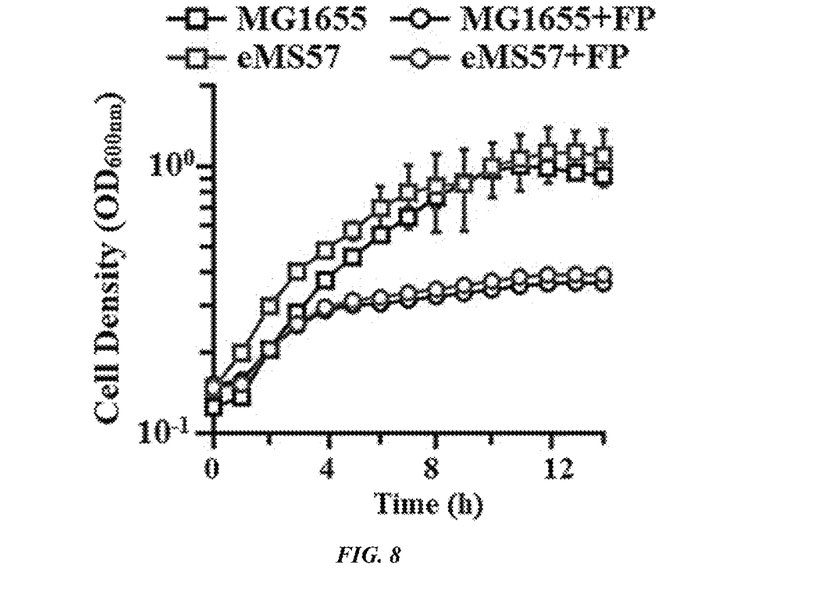
FIG. 8 shows a pyruvate uptake system of in eMS57, examined by results of pyruvate analog (3-fluoropyruvate; FP) assay, in which PDH indicates pyruvate dehydrogenase, and error bars indicate standard deviation.

As a result, eMS57 excreted approximately 9-fold higher extracellular pyruvate than MG1655 (FIG. 7). It was confirmed that eMS57 grows well when fed with pyruvate as a sole carbon source, and its growth was inhibited by 3-flouro-pyruvate, similar to MG1655, indicating that eMS57's pyruvate uptake function is intact (FIG. 8).

These results indicate that eMS57 has excellent pyruvate uptake and export functions, thereby exhibiting excellent productivity.

Example 5. Examination of Protein Production Capacity of eMS57

Protein translation efficiency of eMS57 and protein production capacity thereby were examined.

First, to examine the protein production capacity, a fluorescence protein (mRFP1) was used as a target protein.

In detail, a gene encoding the fluorescence protein was introduced into eMS57 or MG1655 strain, and protein expression of the gene, i.e., fluorescence intensity was examined.

Figure 9:
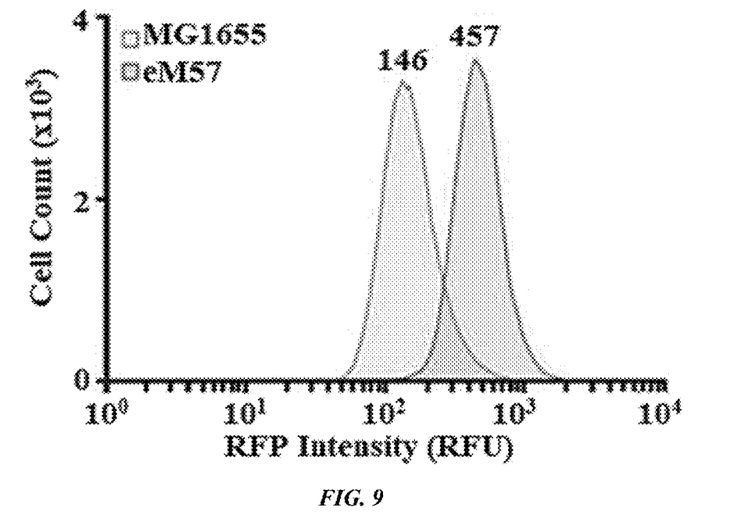
FIG. 9 is a chromatogram showing the results of measuring fluorescence protein production of MG1655 and eMS57 by flow cytometry.

As a result, eMS57 showed 3.1-fold higher fluorescence intensity than MG1655 (FIG. 9).

Meanwhile, microbial translation exhibits a phenomenon called 'post-transcriptional buffering' or 'translational buffering', which means that the amount of transcriptome dynamically changes while maintaining ribosome-occupied mRNA at a constant level. As a result, the translational efficiency (TE), calculated by dividing ribosome-bound transcript levels by the total amount of the transcript, decreases as the amount of the transcript increases. This suggests the presence of complex regulation at the post-transcriptional level in bacteria.

Accordingly, to elucidate the mechanism of increased protein production capacity of eMS57, transcriptome sequencing (RNA-Seq) and ribosome profiling (Ribo-Seq) were performed.

In detail, transcriptome sequencing was performed by the following method. Samples (10 ml) were harvested from the media at the mid-log growth phase ($OD_{600mm}$ ~0.55 for MG1655, ~0.50 for eMS57). Thereafter, total RNA was isolated using the RNASnap™ method, and treated with DNase I to remove DNA contaminants. Then, the RNA samples were purified with phenol-chloroform-isoamyl alcohol extraction followed by ethanol precipitation. Ribosomal RNA (rRNA) was removed from total RNA samples using a Ribo-Zero rRNA Removal Kit. RNA sequencing libraries were constructed from rRNA-subtracted RNA using a TruSeq Stranded mRNA LT Sample Prep Kit (Illumina). Constructed sequencing libraries were quantified using a Qubit dsDNA HS Assay Kit (Thermo). Quality of libraries was analyzed using a TapeStation 2200 (Agilent) equipped with High Sensitivity D1000 Screen Tape (Agilent). The sequencing libraries were sequenced using a MiSeq Reagent Kit v2 (Illumina).

Meanwhile, ribosome profiling was conducted without tRNA removal 50 ml of *E. coli* culture was collected after 5 min treatment of chloramphenicol (34 mg/ml) at exponential growth phase. Cells were frozen with 0.5 ml of lysis buffer (1% Triton X100, 34 µg/ml chloramphenicol, 133 mM of NaCl, 4.75 mM of $MgCl_2$, and 19 mM of Tris-HCl, pH 7.5) and lysed by pestle and mortar. Then, supernatant was isolated and treated with NEB (micrococcal nuclease). Polysomes were recovered from MNase-digested sample using Illustra MicroSpin S-400 HR Columns (GE Healthcare) followed by phenol:chloroform:isoamyl alcohol extraction. Ribosomal RNA was removed using a RiboZero rRNA Removal Kit (Illumina). rRNA-subtracted RNA samples were phosphorylated using NEB (T4 Polynucleotide Kinase) and purified with RNeasy MinElute columns (Qiagen). Sequencing libraries were prepared from phosphorylated RNA samples using the NEBNext Small RNA Library Prep Set for NEB. Next generation sequencing was performed by the ChunLab (Seoul. South Korea) with high output mode using V4 sequencing-by-synthesis reagent on a HiSeq 2500 instrument.

Figure 10A:
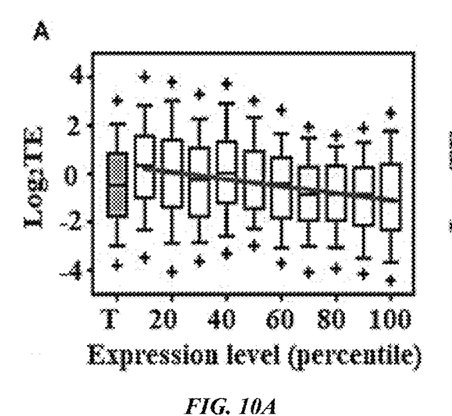
FIG. 10A-B is a graph showing translational buffering of MG1655 (A) and eMS57 (B) and translational efficiency thereby, in which translational buffering of 762 genes was ranked in percentile according to the gene expression level of each strain, T represents the total genes, and the red line represents the linear regression of the mean value of the percentiles.
Figure 10B:
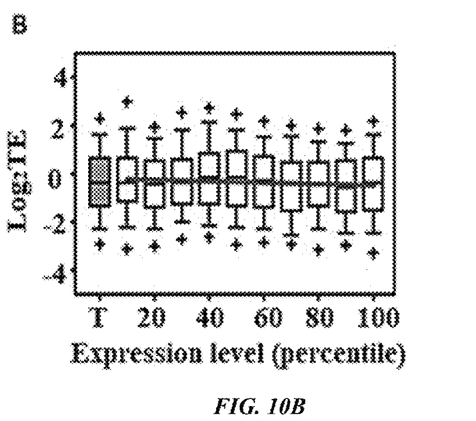

As a result, it was confirmed that the translational efficiency of MG1655 was decreased due to translational buffering, although transcription of the gene occurred well. In contrast, eMS57 exhibited no translational buffering, because translational efficiency remained constant regardless of the gene expression and the resulting transcript level (FIG. 10). For example, in the case of MurQ (N-acetylmuramic acid 6-phosphate etherase) gene. MG1655 and eMS57 showed similar expression levels of 24.8% and 23.9%, respectively. However, eMS57 showed much higher translational efficiency. Further, a higher expression level of gapA (encoding G3P dehydrogenase) gene was observed in MG1655 than eMS57, but they showed similar translational efficiency of 98.8% and 98.7%, respectively (FIG. 11).

These results indicate that even though the gene is well expressed and the amount of the transcript is increased, the productivity of the protein is increased only when the translation efficiency of translating the corresponding transcript is increased, and eMS57 having the high translational efficiency may be usefully applied in the production of a target protein.

Example 6. Comparison of eMS57 and Wild-Type Strain

To examine genes or proteins that contribute to the characteristics of eMS57, which were identified in Examples 2 to 5, genome sequencing and transcriptome analysis were performed.

Figure 12A:
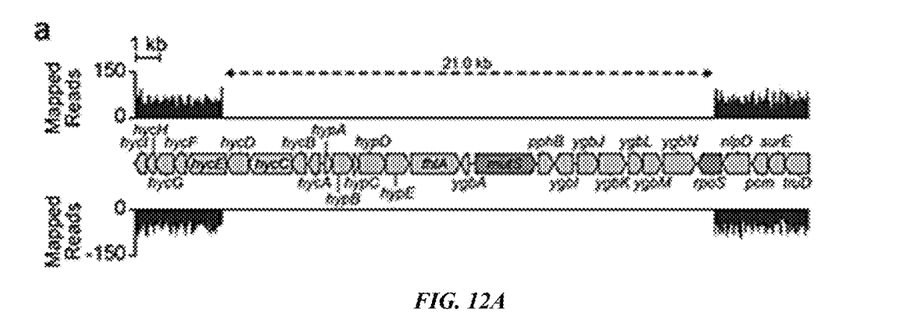
FIG. 12A shows a deletion of the 21-kb region from eMS57 genome.
Figure 12B:
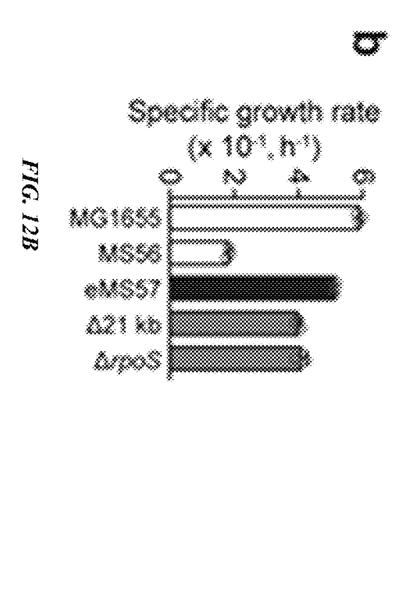
FIG. 12B is a graph showing growth rates of MG1655, MS56, eMS57, and MS56 with a deletion of the genome region (21 kb) deleted from eMS57 or with rpoS deletion.
Figure 12C:
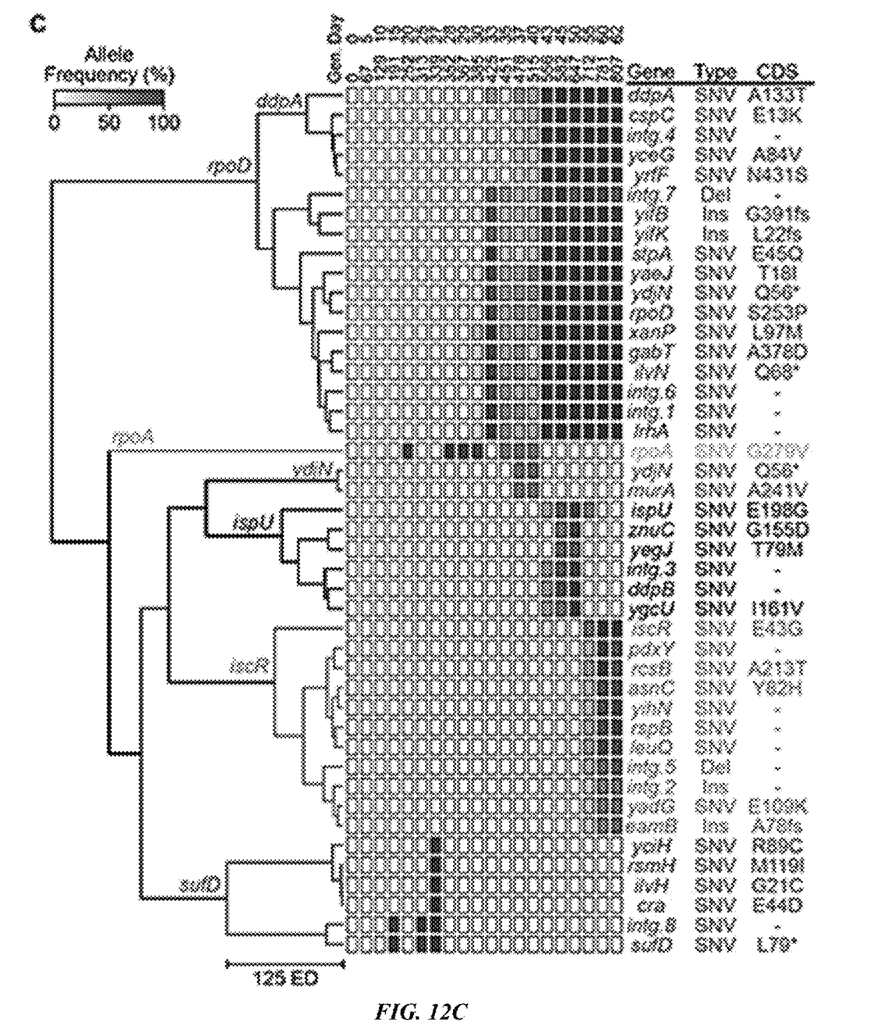
FIG. 12C is a heatmap indicating frequencies of mutations during ALE.

The results of genome sequencing showed that a genomic region of approximately 21 kb was deleted during ALE, and rpoS was included in this region (FIG. 12). As a result of knockout or deletion of rpoS from MS56, eMS57 showed the growth rate of approximately 80% (FIG. 12). Even though rpoS gene contributes to the high growth rate of eMS57, this was not the sole cause of the growth rate. Additionally, it was confirmed that mutations such as SNV (single nucleotide variation), MNV (multi nucleotide variation) and INS (insert)/DEL (deletion) were introduced during ALE (FIG. 12).

Figure 13A:
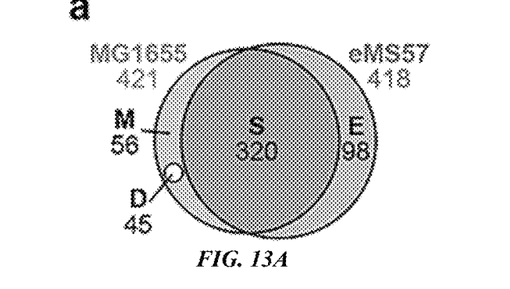
FIG. 13A shows $\sigma^{70}$ binding site (promoter) of MG1655 or eMS57, S represents $\sigma^{70}$ binding sites shared by wild-type (MG1655) and mutant (eMS57), D represents regions deleted from eMS57, M represents wild-type, and E represents the number of promoters specifically binding to mutants.
Figure 13B:
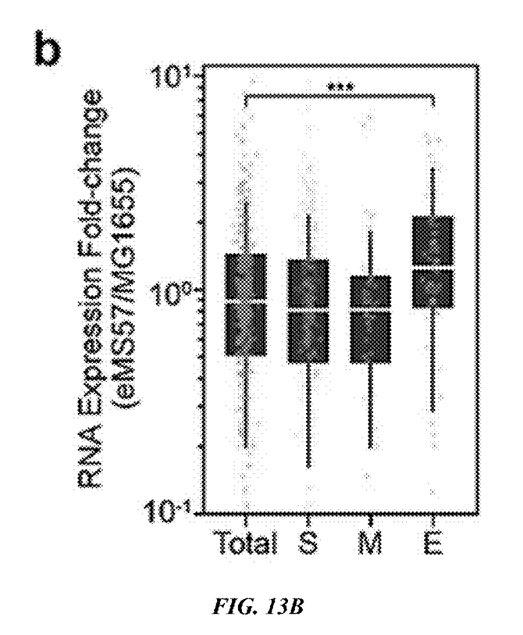
FIG. 13B shows changes of gene expression according to $\sigma^{70}$ mutation.
Figure 13C:
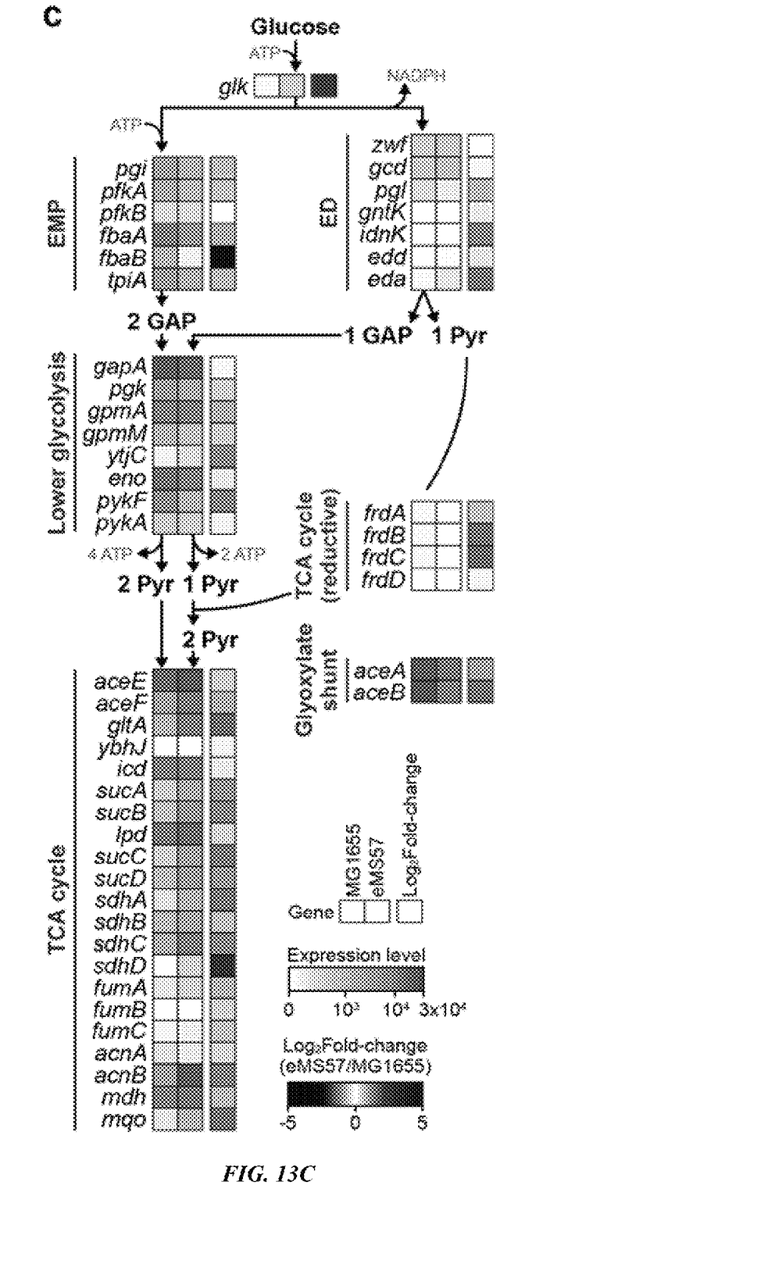
FIG. 13C shows glycolysis and TCA cycle expression levels.

Subsequently, transcriptomic changes were examined by ChIP-Seq and RNA-Seq. In detail, activities of $\sigma^{70}$ in which serine at position 253 was mutated to proline due to SNV of rpoD gene, confirmed by the genome sequencing, and $\sigma^{70}$ of MG1655 (wild-type $\sigma^{70}$) were measured. As a result, the mutant $\sigma^{70}$ showed high binding specificity to E promoter while the specificity to M promoter remained unchanged. It was also determined that the change will affect expression of other genes. Thus, transcriptome analysis was performed, and genes whose expression levels were changed by mutant $\sigma^{70}$ are shown in FIG. 13. It was speculated that this change in expression level may allow eMS57 to adapt to minimal media.

These results suggest that genetic mutations shown in FIGS. 12 and 13 are involved in the characteristics of eMS57.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

DEPOSIT NUMBER

Deposit authority. Korea Research Institute of Bioscience and Biotechnology

Accession Number: KCTC 13699BP

Date of deposit: 2018. 11. 08.

This deposit was made under the Budapest Treaty with the International Depository Authority of Korean Collection for Type Cultures having an address of 181, Ipsin-gil, Jeongeup-si, Jeolllabuk-do 56212, Republic of Korea. This deposit will be maintained at the authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

EFFECT OF THE INVENTION

Despite a small genome size, a novel microorganism of the present disclosure may have a high growth rate, pyruvate production capacity, and protein translation efficiency thereby being usefully applied to industry such as production of recombinant proteins or pyruvate.

What is claimed is:

1. An engineered microorganism comprising the deposited microorganism with Accession No. KCTC13699BP.

2. The engineered microorganism of claim 1, wherein the genome size is no more than 3.6 Mbp.

3. A method of producing pyruvate or a protein, the method comprising the step of culturing the microorganism of claim 2.

4. The engineered microorganism of claim 1, wherein the novel microorganism has a higher growth rate than *E. coli* MS56 strain.

5. A method of producing pyruvate or a protein, the method comprising the step of culturing the microorganism of claim 4.

6. The engineered microorganism of claim 1, wherein the microorganism has a higher pyruvate production capacity than *E. coli* MG1655 strain.

7. A method of producing pyruvate or a protein, the method comprising the step of culturing the microorganism of claim 6.

8. A method of producing pyruvate or a protein, the method comprising the step of culturing the microorganism of claim 1.

9. The engineered microorganism of claim 1, wherein the microorganism has a smaller genome size than *E. coli* MG1655 strain.

10. The engineered microorganism of claim 1, wherein the microorganism has a smaller genome size than *E. coli* MS56 strain.

* * * * *